United States Patent [19]

Barber et al.

[11] 4,000,461

[45] Dec. 28, 1976

[54] R-WAVE DETECTOR

[75] Inventors: Ronald Charles Barber, Portland; Don Loren Clark, Hillsboro

[73] Assignee: Richard James Ballard; Beaverton, Textronix, Inc., Beaverton, Oreg.

[22] Filed: Oct. 4, 1973

[21] Appl. No.: 403,689

[52] U.S. Cl. .................. 324/102; 128/2.05 A; 128/2.06 A; 324/77 A

[51] Int. Cl.$^2$ ............. G01R 19/00; A61B 5/02

[58] Field of Search ........... 324/102, 77 A, 77 R, 324/78 D; 128/2.06 F, 2.05 T, 2.05 A, 2.06 A

[56] References Cited

UNITED STATES PATENTS

| | | | |
|---|---|---|---|
| 2,801,629 | 8/1957 | Edmark, Jr. | 128/2.05 T |
| 2,918,054 | 12/1959 | Goelkasian | 128/2.05 T |
| 3,534,282 | 10/1970 | Day | 128/2.06 A |
| 3,575,162 | 4/1971 | Gaarder | 128/2.05 T |
| 3,590,811 | 7/1971 | Harris | 128/2.06 A |
| 3,612,041 | 10/1971 | Ragsdale | 128/2.06 A |
| 3,616,791 | 11/1971 | Harris | 128/2.06 A |
| 3,646,931 | 3/1972 | Phelps et al. | 128/2.05 T |
| 3,742,938 | 7/1973 | Stern | 128/2.05 T |
| 3,878,833 | 4/1975 | Arneson et al. | 128/2.06 A |

*Primary Examiner*—Palmer C. Demeo
*Assistant Examiner*—Ernest F. Karlsen
*Attorney, Agent, or Firm*—George T. Noe

[57] ABSTRACT

An electronic system is disclosed which examines the first derivative of an applied electrocardiographic (ECG) signal, recognizes the R-wave event therefrom, and discriminates against signal components which lie outside predetermined signal parameters in producing a rectangular pulse output. In addition, muscle artifact and pacers are discriminated against. The system includes an automatic gain control to eliminate the need for operator controls.

22 Claims, 3 Drawing Figures

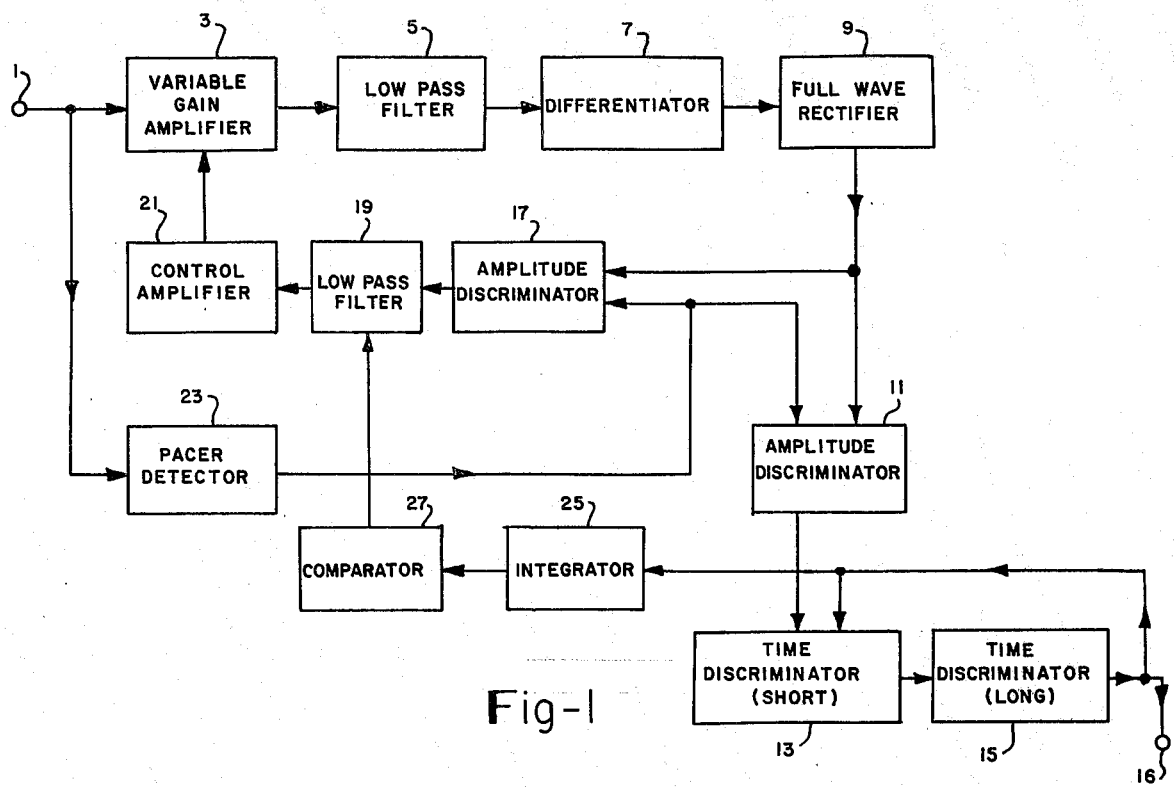
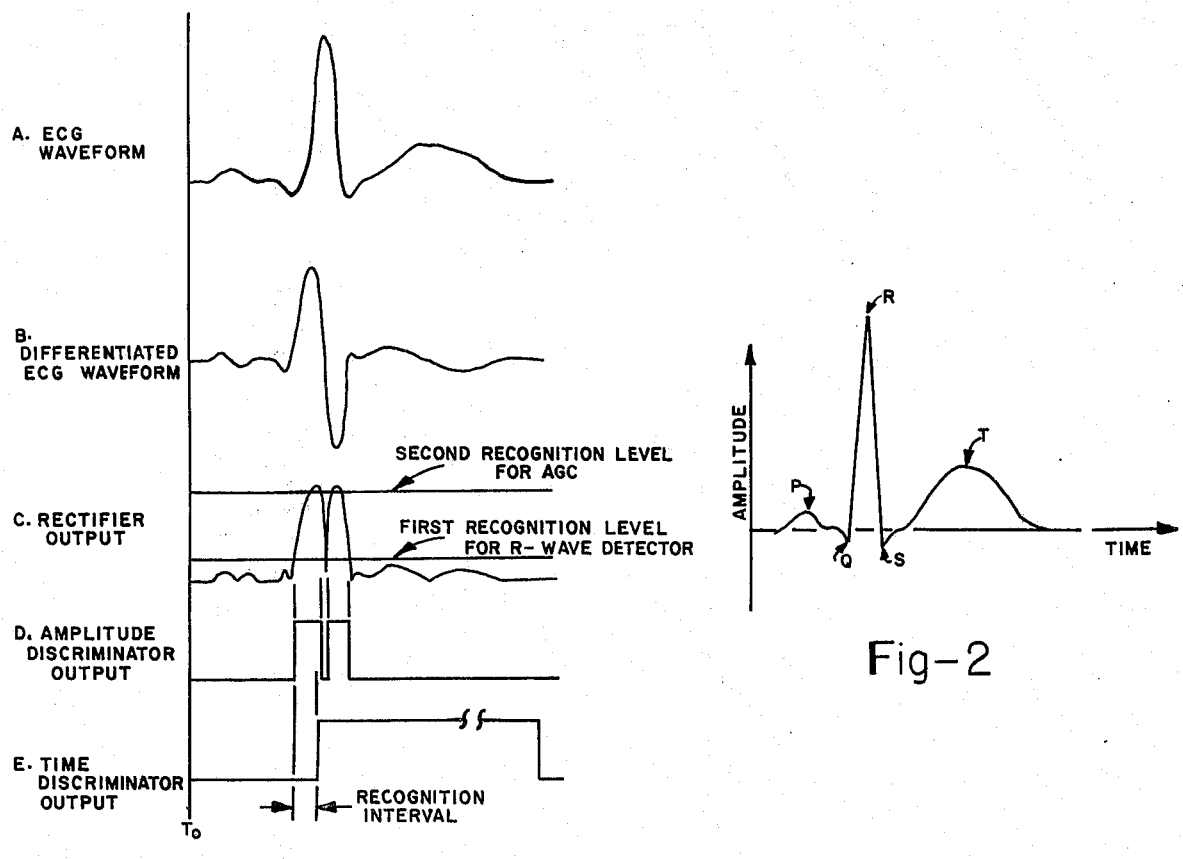

R-WAVE DETECTOR

BACKGROUND OF THE INVENTION

In electrocardiographic measuring and monitoring systems, it is desirable to provide a two-dimensional display of time-varying ECG signals on the screen of a cathode ray tube. Typically, the horizontal (X) axis of the display represents time while the vertical (Y) axis represents signal amplitude. It is essential in producing a meaningful display that the horizontal sweeping of the beam across the cathode ray tube screen be synchronized with the ECG signals in a manner similar to that of a triggered oscilloscope.

It is also desirable in such systems to provide an alarm in the event of heart malfunction. Reliable detection of the electrical signal related to heart pumping action is essential both to the implementation of the synchronized display and to the measurement of heart beat rate to monitor the condition of the heart. However, it is extremely difficult to obtain reliable triggering and heartbeat information in the presence of motion artifacts, muscle noise, fluctuations in R-wave amplitude, and electronic heart pacer devices.

In previous systems, it has been a common practice to employ a level comparator to provide a trigger for the sweep and for the rate detector whenever the ECG signal amplitude surpasses a predetermined amplitude level. The R wave is normally of greater amplitude than any other component of the ECG cycle, and therefore is generally used for such triggering and rate detection purposes. However, a major drawback to this scheme is imposed in the presence of electrical and muscle noise on the ECG signal, which may have sufficient amplitude to inadvertently effect triggering of the sweep. Furthermore, devices such as pacers continue to operate and produce a triggered sweep long after a patient has expired. Therefore, it is imperative in monitoring situations such as in intensive care units that only the physiologically-produced signals be recognized.

SUMMARY OF THE INVENTION

According to the present invention, electrocardiographic signals are applied to a system of discriminators for detection of the R-wave event. In most ECG signals, the QRS complex thereof has the characteristic of exhibiting the greatest time rate of change of signal voltage, hereinafter referred to as $dv/dt$, of any portion of the signal which has a unidirectional slope lasting 15 milliseconds or more. Muscle artifacts and pacers may have greater $dv/dt$, but the time duration is shorter in any one slope. P and T waves may have a longer time duration in one slope, but have much lower $dv/dt$.

The ECG signals are first amplified to a suitable level and then may be passed through a low-pass filter to eliminate much of the highfrequency muscle artifact components. A differentiator then accentuates slopes having a $dv/dt$ greater than a predetermined value while attenuating components having a lower $dv/dt$. A full-wave rectifier may be employed to eliminate polarity sensitivity. The rectified signal is then applied to an amplitude discriminator, which rejects the lower amplitude components and produces pulses corresponding in time duration to the accepted signal slopes, which have the greatest $dv/dt$ and greatest time duration. The pulses are finally applied to a time discriminator which rejects pulses having a duration shorter than a predetermined time, and producing a rectangular pulse output when a qualifying pulse is recognized. Because of ECG signal characteristics, this rectangular pulse is coincident with one of the slopes in the R-wave component. The time discriminator, once accepting a qualifying slope, locks out further inputs for a predetermined time interval to prevent multiple pulse output in the event that two or more slopes within the Q to T interval may qualify.

The system may include an automatic gain control for the amplifier to which the ECG signals are applied in order to maintain a substantially consistent signal proportion for R-wave detection when the ECG signal is fluctuating or differs in amplitudes from patient to patient. A novel approach in this system is to provide a selective automatic gain control by applying the first derivative of the ECG signal to a second amplitude discriminator, which produces a control voltage in response to the time duration of a portion of the differentiated R wave. The control voltage is applied to a control amplifier to appropriately vary the gain of the ECG amplifier. In this manner, only the R-wave component of the ECG signal is affected by the automatic gain control. In addition, the automatic gain control may include a provision to cause the gain of the ECG amplifier to rapidly increase to its maximum value in the event of loss of an output signal from the system, so that the system can quickly recover to detect a low-amplitude ECG signal.

A pacer detector may be employed to detect signals having a $dv/dt$ greater than that which could be physiologically produced. A pulse coincident with the detected pacer pulse is applied to the amplitude discriminators to block entry of the pacer signals into the discriminators.

It is therefore one object of the present invention to detect the R-wave event in an applied electrocardiographic signal.

It is another object of the present invention to provide a rectangular pulse output coincident with the R-wave event in an electrocardiographic signal.

It is a further object of the present invention to provide reliable triggering for a physiological monitor on a beat-to-beat basis.

It is yet another object of the present invention to provide reliable heart beat rate informaton for purposes of heart malfunction detection.

It is yet a further object of the present invention to detect the R-wave event in an electrocardiographic signal in the presence of a pacer signal.

It is still another object of the present invention to detect the R-wave event in an electrocardiographic signal in the presence of motion artifact and muscle noise.

It is still a further object of the present invention to provide an R-wave detector which is insensitive to signal polarity.

It is another object of the present invention to provide an R-wave detector which will automatically respond to ECG signals of varying amplitudes.

It is a further object of the present invention to provide a novel automatic gain control to eliminate the necessity of operator controls.

Further objects, features, and advantages will be apparent from consideration of the following description taken in conjunction with the accompanying drawings.

BRIEF DESCRIPTION OF THE DRAWINGS

FIG. 1 is a block diagram of the R-wave detector system according to the present invention;

FIG. 2 illustrates a typical electrocardiographic waveform, identifying the P, Q, R, S, and T waves; and FIG. 3 is a waveform ladder diagram showing the time relationship of various waveforms throughout the system of FIG. 1.

DETAILED DESCRIPTION OF THE INVENTION

Turning now to the drawings, FIG. 1 shows a block diagram of the system according to the present invention. Each block of the block diagram comprises circuitry well known in the art, obviating an exhaustive dissertation of circuit operation. Instead, each block will be discussed in accordance with its contribution to the overall system.

An electrocardiographic waveform similar to that shown in FIG. 2 is applied to an input terminal 1. The waveform shown in FIG. 2 is a typical ECG waveform whose amplitude is plotted against time. The P, Q, R, S, and T components are identified, and it can be seen that the R wave has an amplitude and time rate of change greater than any other portion of the waveform. For this description, however, the ladder diagram of FIG. 3 will be used to show the waveform relationships throughout the system, and therefore the ECG waveform is shown in expanded time scale in FIG. 3A.

This ECG waveform may be amplified by a suitable variable gain amplifier 3 and then may be passed through a low pass filter 5 to remove extraneous signals having frequency components higher than those which would be considered part of the ECG waveform. In this manner, ECG waveforms of varying amplitudes can be amplified to a substantially consistent level, and much of the motion artifact and muscle noise which may be riding on the ECG waveform may be removed.

The ECG waveform is then applied to a differentiator 7, which may be a conventional resistive-capacitive differentiating network, to produce the first derivative of the ECG signal. The differentiated ECG waveform, shown in FIG. 3B, is then applied to a full-wave rectifier 9 to produce a waveform having components all of one polarity, for example, the positive components shown in FIG. 3C.

The rectified first deriviative of the ECG signal is then applied to amplitude discriminator 11, which may for example be an amplifier which is normally cut off and then biased into conduction when the amplitude of the rectified and differentiated signal exceeds a predetermined level. This predetermined level, hereinafter referred to as the recognition level, is shown as the first recognition level in FIG. 3C. The first recognition level is chosen to reject lower-amplitude components of the rectifier output. When the rectifier output exceeds the recognition level, the amplitude discriminator 11 produces an output voltage in the form of a pulse of a series of pulses as shown in FIG. 3D.

The output pulses from amplitude discriminator 11 are applied to a short time discriminator 13. The time discriminator 13 will act only on pulses having a time interval which exceeds a predetermined recognition interval, rejecting any pulse which has a duration shorter than the duration of the slope of a typical R wave. The recognition interval, then, can be in the range of from about 5 to 25 milliseconds, and any pulse having a time duration which exceeds the recognition interval will produce an output from discriminator 13. As can be seen in FIG. 3E, the rising portion of the time discriminator output is nearly coincident with the peak of the R wave of the ECG waveform shown in FIG. 3A.

The output of short time discriminator 13 may be applied to long time discriminator 15, which produces a voltage in the form of a rectangular pulse in response to the output from discriminator 13. Long time discriminator 15 operates for a time interval which is approximately the length of time required for one complete Q-through T-wave cycle which may vary from 100 to 250 milliseconds. The rectangular pulse output is available at output terminal 16, and may also be applied to short time discriminator 13 to inhibit further pulses from amplitude discriminator 11 once the time discriminator 13 has recognized a qualifying pulse during a single ECG waveform cycle. The time interval of long time discriminator 15 may be adjusted to accomodate the maximum expected heart bear rates.

The R-wave detection system according to the present invention may include an automatic gain control to electronically vary the gain of variable gain amplifier 3. The automatic gain control includes a second amplitude discriminator 17 connected to receive the rectified first derivative of the ECG waveform from rectifier 9, a low pass filter 19 through which the output of the amplitude discriminator 17 is passed, and a control amplifier 21 which produces a control voltage in response to the output of the low pass filter 19 to electronically control the gain of amplifier 3.

Since a consistent signal amplitude from one heart beat to another is desired for the first amplitude discriminator 11 to act upon, the recognition level of amplitude discriminator 17 for the automatic gain control is set to approximately the desired amplitude, or slightly less. FIG. 3C shows the second recognition level superimposed on the rectifier output waveform. The amplitude discriminator 17 will produce an output when the amplitude of the signal from rectifier 9 exceeds the second recognition level. If the second recognition level is not reached, there is no output from amplitude discriminator 17. Under these conditions, the control amplifier 21 increases the gain of variable gain amplifier 3. Eventually, the amplitude of the rectifier 9 output will surpass the recognition level of amplitude discriminator 17, and an output will be produced and passed through the low pass filter 19 to hold the input of control amplifier 21 at the level required to maintain the gain of variable gain amplifier 3 at a level which will produce a consistent signal amplitude from beat to beat. Low pass filter 19 averages the output of amplitude discriminator 17 between beats of ECG signals so as to provide the proper level restoration at the input of control amplifier 21 to maintain the proper amount of gain of variable gain amplifier 3.

In addition to the foregoing, the automatic gain control may include a provision to cause the variable gain amplifier 3 to rapidly increase to its maximum value if the rectangular pulse output from the system falls below a predetermined rate. Loss of an output is indicative of a loss of the ECG signal. This provision may include an integrator 25 and a comparator 27 connected between the system output terminal 16 and the low pass filter 19. Integrator 25 receives the rectangular pulses produced by time discriminator 15 and produces a sawtooth voltage which is reset to zero with the occurrence of each pulse and rises slowly between pulses. Comparator 25 which may be a conventional comparator having a predetermined reference level, receives the sawtooth voltage from integrator 25. If the output pulses from discriminator 15 cease or fall below a predetermined rate, which may be, for example, 10 to 20 output pulses per minute, the sawtooth voltage from integrator 25 will rise to the reference level of comparator 27, causing comparator 27 to produce an output which is applied through a portion of the low pass filter 19 to control amplifier 21. Under this condition, the input to control amplifier 21 is of a level which will cause the gain of variable gain amplifier 3 to immediately increase to its maximum value, facilitating a high-sensitivity system to detect a low-amplitude ECG signal if such is available.

The R wave detection system according to the present invention may also include a circuit for detecting the presence of a pacer or similar device and prevent this device from having any affect on the system. The ECG waveform at terminal 1 may also be applied to pacer detector 23. Pacer detector 23 may include, for example, a frequency selective amplifier which responds only to signals having a time rate of change greater than that which could be physiologically produced, and a switch which produces a short-duration output pulse coincident with such a detected signal. The output from detector 23 is applied simultaneously to amplitude discriminator 11 and amplitude discriminator 21 to block entry of the rectifier 9 output into the discriminators. Thus, the pacer has no effect on the operation of the system to detect R waves.

It will be obvious to those skilled in the art that many changes may be made in the details of the above-described preferred embodiment of the present invention without departing from the spirit of the invention. For example, there are many circuit configurations that can be arranged to perform the amplitude and time discriminator functions.

We claim:

1. The method of detecting the R wave in an electrocardiographic waveform including P, Q, R, S, and T waves, comprising:
    reshaping said electrocardiographic waveform to provide wave components having shape characteristics predetermined in accordance with the shape characteristics of said electrocardiographic waveform so that only a reshaped wave component corresponding to said R wave has an amplitude greater than a predetermined level and a time duration greater than a predetermined period;
    selecting reshaped wave components having an amplitude greater than said predetermined level and a time duration greater than said predetermined period; and
    producing output pulses at the end of said predetermined period in response to said selected wave components, whereby said output pulses correspond to said R wave.

2. The method according to claim 1 wheein the reshaping step is performed by differentiating said electrocardiographic waveform and rectifying the first derivative thereof.

3. The method according to claim 1 wherein the selecting step is performed by first discriminating against reshaped wave components having an amplitude less than said predetermined level and producing first signals having time durations corresponding to wave components exceeding said predetermined level, and then discriminating against first signals having a time duration less than said predetermined period and producing second signals in response to first signals having time durations exceeding said predetermined period.

4. An electronic system for detecting the R wave in an electrocardiographic waveform including P, Q, R, S, and T waves, comprising:
    means for reshaping said electrocardiographic waveform to provide wave components having shape characteristics determined in accordance with the shape characteristics of said electrocardiographic waveform so that only a reshaped wave component corresponding to said R wave has an amplitude greater than a predetermined level and a time duration greater than a predetermined period; and
    means for selecting reshaped wave components having an amplitude greater than said predetermined level and a time duration greater than said predetermined period.

5. The system according to claim 4 wherein said means for reshaping said electrocardiographic waveform includes differentiator means and rectifier means.

6. The system according to claim 4 wherein said means for selecting reshaped wave components includes amplitude discriminating means and time discriminating means, said amplitude discriminating means discriminating against reshaped wave components having an amplitude less than said predetermined level and producing first pulses having time durations corresponding to wave components exceeding said predetermined level, and said time discriminating means discriminating against first pulses having a time duration less than said predetermined period and producing second pulses in response to first pulses having time durations exceeding said predetermined period.

7. The system according to claim 4 including low pass filter means for removing signal components having a frequency higher than a predetermined frequency limit from said electrocardiographic waveform.

8. The system according to claim 4 including automatic gain control means for maintaining a consistent wave component amplitude for said selecting means irrespective of varying electrocardiographic waveform amplitudes.

9. The system according to claim 8 wherein said automatic gain control means includes means for detecting the amplitude of said wave components and developing a control signal in response thereto, and a variable gain amplifier responsive to said control signal to vary the gain thereof.

10. The system according to claim 9 wherein said means for detecting the amplitude of said wave components and developing a control signal in response thereto includes an amplitude discriminator, a low pass filter, and an amplifier.

11. The system according to claim 9 wherein said automatic gain control means includes means for increasing the gain of said variable gain amplifier to maximum when no reshaped wave components are selected within a predetermined time period.

12. The system according to claim 11 wherein said means for increasing the gain of said variable gain amplifier to maximum when no reshaped wave components are selected within a predetermined time period includes an integrator and a comparator connected between said selecting means and said variable gain amplifier.

13. The system according to claim 4 including detector means for detecting a signal having a frequency component greater than could be physiologically produced in said electrocardiographic waveform, said detector means generating a control pulse coincident with said signal to interrupt said selecting means during said signal.

14. An electronic system for detecting the R wave in an electrocardiographic waveform including P, Q, R, S, and T waves, comprising:
an input terminal for receiving said electrocardiographic waveform;
means for reshaping said electrocardiographic waveform to provide wave components having shape characteristics determined in accordance with the shape characteristics of said electrocardiographic waveform so that only a reshaped wave component corresponding to said R wave has an amplitude greater than a predetermined level and a time duration greater than a predetermined period;
an amplitude discriminator for rejecting reshaped wave components below a predetermined level and producing a signal having a time duration coincident with reshaped wave conponents above said predetermined level; and
a time discriminator for rejecting signals from said first amplitude discriminator having a time duration shorter than a predetermined period and producing an output pulse responsive to a signal having a time duration longer than said predetermined period, whereby said output pulse corresponds to said R wave.

15. The system according to claim 14 wherein said reshaping means includes a differentiator and a rectifier, said reshaped wave components being the rectified first derivative of said electrocardiographic waveform.

16. The system according to claim 14 including a second time discriminator responsive to said output pulse to prevent said first time discriminator from accepting a second signal during a second predetermined period.

17. The system according to claim 14 including a low pass filter between said input terminal and said reshaping means, said low pass filter removing signal components having a frequency higher than a predetermined frequency limit from said electrocardiographic waveform.

18. The system according to claim 14 including automatic gain control means for maintaining a consistent wave component amplitude for said amplitude discriminator irrespective of varying electrocardiographic waveform amplitudes.

19. The system according to claim 18 wherein said automatic gain control means includes a second amplitude discriminator for receiving said reshaped wave components and producing an output when a second predetermined level is exceeded by said components, an low pass filter for averaging the output voltage of said second amplitude discriminator, a control amplifier for receiving the average voltage from said low pass filter and developing a control voltage in response thereto, and a variable gain amplifier connected between said input terminal and said reshaping means, the gain of said variable gain amplifier being controlled by said control voltage.

20. The system according to claim 19 wherein said automatic gain control means includes means for developing a second control voltage if no output pulses occur within a predetermined time interval, said second control voltage causing the gain of said variable gain amplifier to increase to its maximum value.

21. The system according to claim 20 wherein said means for developing a second control voltage includes an integrator adapted to receive said output pulses, and a comparator for producing an output when the voltage from said integrator reaches a predetermined reference level.

22. The system according to claim 14 including detector means for detecting the presence of an electronic pacer signal in said electrocardiographic waveform, said detector means generating a control pulse coincident with said pacer to cancel the output of said reshaping means during said pacer signal.

* * * * *

UNITED STATES PATENT AND TRADEMARK OFFICE
CERTIFICATE OF CORRECTION

PATENT NO. : 4,000,461
DATED : December 28, 1976
INVENTOR(S) : Barber/Clark/Ballard It is certified that error appears in the above-identified patent and that said Letters Patent are hereby corrected as shown below:

Inventors: (Item 75) "Ronald Charles Barber, Portland;
Don Loren Clark, Hillsboro"

Should be: -- Ronald Charles Barber, Portland;
Don Loren Clark, Hillsboro;
Richard James Ballard, Beaverton--

Assignee: (Item 73) "Richard James Ballard; Beaverton,
Tektronix, Inc.
Beaverton, Oreg."

Should be: -- Tektronix, Inc.
Beaverton, Oreg.--

Column 1, Line 13, "signals" should be --signal--
Column 3, Line 54, "of a pulse of a" should be --of a pulse or a--
Column 4, Line 15, "heart bear" should be --heart beat--
Column 5, Line 54, "wheein" should be --wherein--
Column 8, Line 14, "an low pass" should be --a low pass--
Column 8, Line 38, "said pacer to" should be --said pacer signal to--

Signed and Sealed this

Sixth Day of September 1977

[SEAL]

Attest:

RUTH C. MASON
*Attesting Officer*

LUTRELLE F. PARKER
*Acting Commissioner of Patents and Trademarks*